US00PP18243P2

(12) United States Plant Patent
Eggleton

(10) Patent No.: US PP18,243 P2
(45) Date of Patent: Nov. 20, 2007

(54) ***LAVANDULA* PLANT NAMED 'SUGARBERRY RUFFLES'**

(50) Latin Name: *Lavandula stoechas*
Varietal Denomination: Sugarberry Ruffles

(76) Inventor: Steven Eggleton, 3 Harris Rd., Wonga Park, Melbourne, Vic 3115 (AU)

( * ) Notice: Subject to any disclaimer, the term of this patent is extended or adjusted under 35 U.S.C. 154(b) by 14 days.

(21) Appl. No.: 11/435,435

(22) Filed: May 16, 2006

(51) Int. Cl.
*A01H 5/00* (2006.01)

(52) U.S. Cl. ..... Plt./226
(58) Field of Classification Search ..... Plt./226
See application file for complete search history.

(56) References Cited

PUBLICATIONS

UPOV ROM GTITM Computer Database GTI Jouve Retrieval Software 2006/04 Citation for Sugarberry Ruffles.*

* cited by examiner

*Primary Examiner*—Wendy C. Haas

(57) ABSTRACT

A new cultivar of *Lavandula* plant named 'SUGARBERRY RUFFLES' that is characterized by early and repeat flowering, dense plant habit, short peduncle length, and fragrant flower spikes with medium length sterile bracts that are mid-pink in color. In combination these traits set 'SUGARBERRY RUFFLES' apart from all other existing varieties of *Lavandula* known to the inventor.

2 Drawing Sheets

Genus: *Lavandula.*
Species: *stoechas.*
Denomination: 'SUGARBERRY RUFFLES'.

BACKGROUND OF THE INVENTION

The present invention relates to a new and distinct cultivar of lavender known botanically as *Lavandula stoechas* and hereinafter referred to by the cultivar name 'SUGARBERRY RUFFLES'.

The new *Lavandula* cultivar named 'SUGARBERRY RUFFLES' is one individual selection in the Australian lavender 'Ruffles Series', that resulted from a formal breeding program. The breeding program was established in November 2001 and conducted by the inventor, at the inventor's nursery in Victoria, Australia. The inventor, a specialist in the genus *Lavandula,* selected 'SUGARBERRY RUFFLES' in 2003. Selection was based on a combination of repeat flowering, dense plant habit, mid-pink sterile bract color, medium sterile bract length, and short peduncle length.

'SUGARBERRY RUFFLES' is a selection arising from the controlled cross-pollination of *Lavandula stoechas* 'Kew Red' (unpatented) as the female parent, and *Lavandula stoechas* 'Pukehou' (unpatented) as the male parent. Cross-pollination of the parent plants took place in Park Orchards, Victoria, Australia in November 2001. From this cross the F1 generation was raised in February 2002 and grown to flowering maturity in September 2002. At this stage the F1 generation was self-pollinated and the seed sown in February 2003. From these F2 seedlings a selection was made when the plants had grown to flowering stage in 140 mm. containers.

'SUGARBERRY RUFFLES' is a perennial suitable for use in container and in the landscape. Cultural requirements include full sun, adequate but not excess water, and well-draining soil. Mature height is 60 cm. and mature width is 70 cm. 'SUGARBERRY RUFFLES' exhibits early and repeat flowering, dense plant habit, scented green foliage, short peduncle length, and scented flower spikes with medium length sterile bracts that are mid-pink in color.

The traits that distinguish 'SUGARBERRY RUFFLES' from the female parent 'Kew Red' are sterile bract length, and plant habit. 'Kew Red' exhibits short sterile bract length, and very dense plant habit, whereas 'SUGARBERRY RUFFLES' exhibits longer sterile bracts, and less dense plant habit. The traits that distinguish 'SUGARBERRY RUFFLES' from the male parent 'Pukehou' are peduncle length, plant habit, and sterile bract color. 'Pukehou' exhibits long peduncle length, medium to sparse plant habit, and purple sterile bract color, compared to 'SUGARBERRY RUFFLES' that exhibits short peduncle length, dense plant habit, and sterile bracts that are mid-pink in color.

The new *Lavandula* cultivar, named 'SUGARBERRY RUFFLES' was first asexually propagated by the inventor in 2004. Asexual propagation was accomplished at the inventor's nursery in Australia, and the method utilized was tip cuttings. Since that time 'SUGARBERRY RUFFLES' has been determined stable, and reproduces true to type in successive generations of asexual propagation.

SUMMARY OF THE INVENTION

The following traits have been repeatedly observed and represent the distinguishing characteristics of the new *Lavandula* cultivar named 'SUGARBERRY RUFFLES'. These traits in combination distinguish 'SUGARBERRY RUFFLES' from all other existing varieties of *Lavandula* known to the inventor. 'SUGARBERRY RUFFLES' has not been tested under all possible conditions and phenotypic differences may be observed with variations in environmental, climatic, and cultural conditions, without however, any variance in genotype.

1. 'SUGARBERRY RUFFLES' exhibits dense plant habit.
2. 'SUGARBERRY RUFFLES' exhibits scented flower spikes with sterile bracts that are medium in length and mid-pink in color.
3. 'SUGARBERRY RUFFLES' exhibits early and repeat flowering.
4. 'SUGARBERRY RUFFLES' exhibits fragrant green foliage.
5. 'SUGARBERRY RUFFLES' is one selection in the Australian lavender 'Ruffles Series' that blooms an average of two weeks earlier than many lavenders in commerce.
6. Cultural requirements for 'SUGARBERRY RUFFLES' are full sun, adequate but not excess water and well-draining soil.
7. 'SUGARBERRY RUFFLES' exhibits short peduncle length.
8. 'SUGARBERRY RUFFLES' is 60 cm in height and 70 cm. in width at maturity.
9. 'SUGARBERRY RUFFLES' is asexually propagated utilizing the method of tip and stem cuttings.
10. 'SUGARBERRY RUFFLES' is suitable for use as an ornamental plant is container or in the landscape.
11. 'SUGARBERRY RUFFLES' is hardy to USDA Zone 8.

BRIEF DESCRIPTION OF THE DRAWINGS

The accompanying drawings illustrate the overall appearance of the new *Lavandula* cultivar named 'SUGARBERRY RUFFLES' showing the colors as true as it is reasonably possible to obtain in color reproductions of this type. Color in the drawings may differ from the color values cited in the detailed botanical description, which accurately describe the actual color of the new *Lavandula* variety named 'SUGARBERRY RUFFLES'. The drawings were made of 9-month-old plants greenhouse grown in 16 cm containers.

The drawing labeled

The drawing labeled

Figure 1:
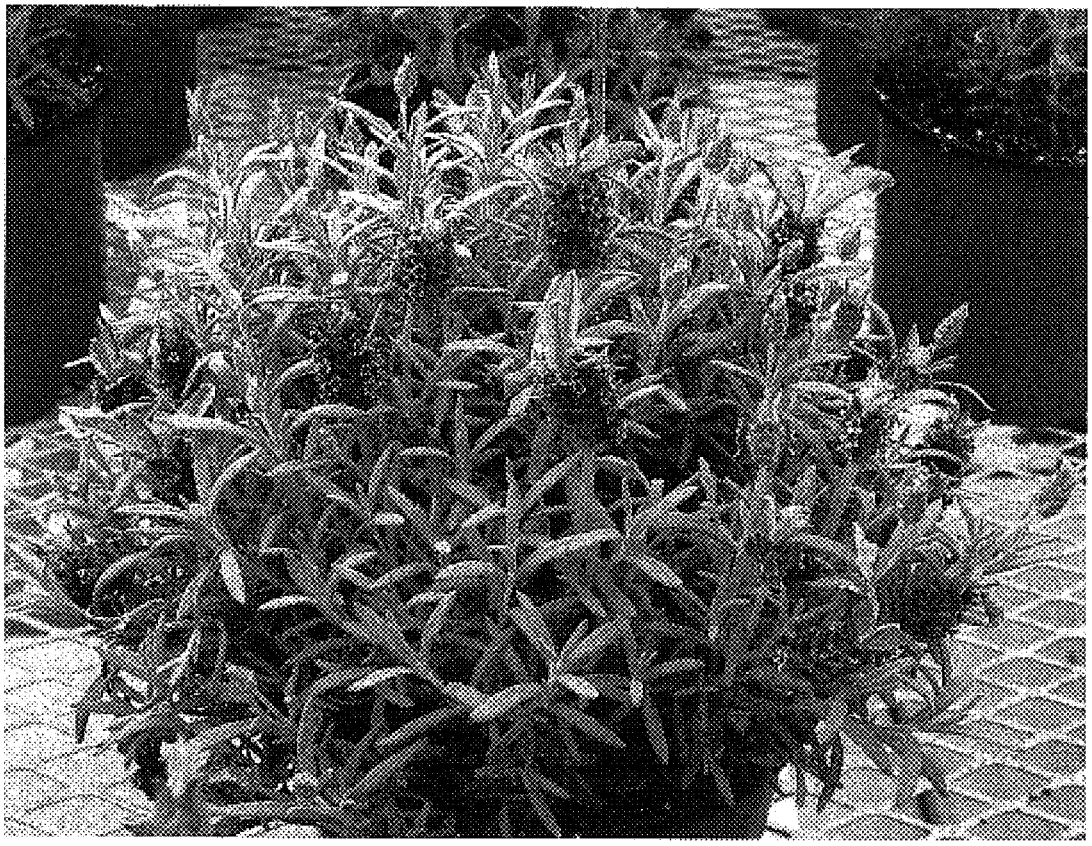
FIG. 1 depicts the plant in bloom from a side perspective.
Figure 2:
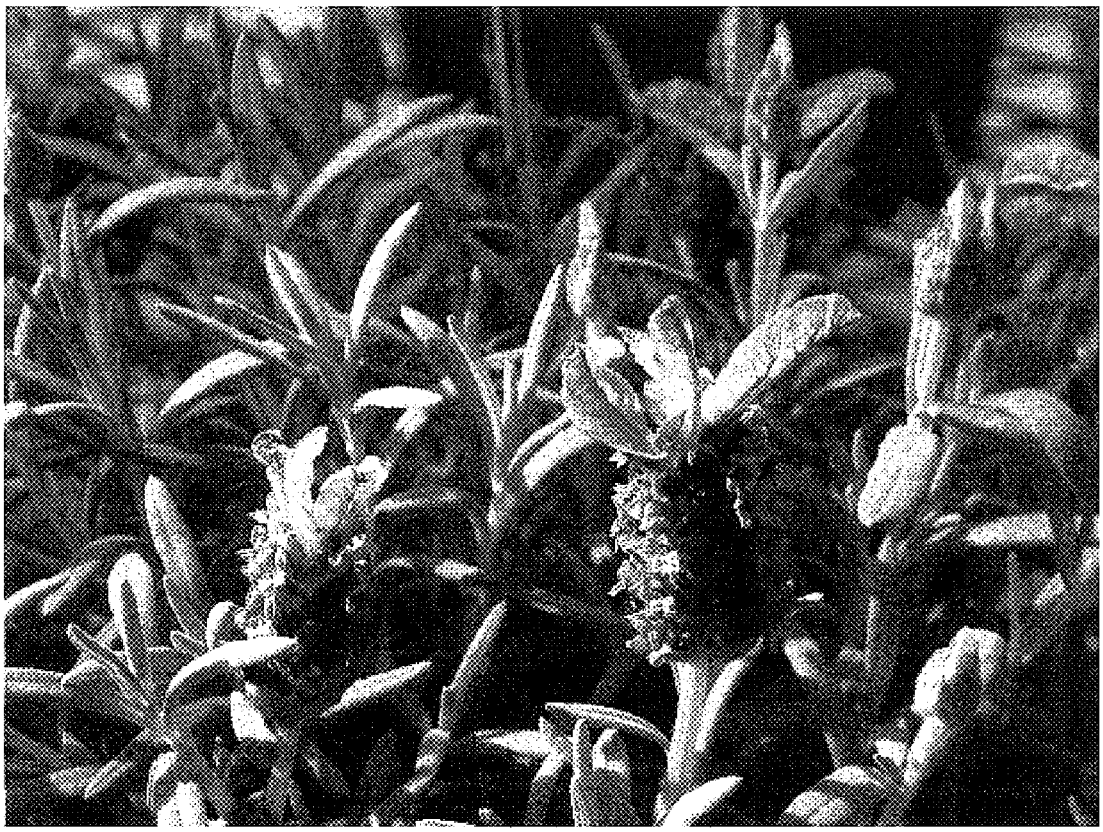
FIG. 2 depicts a close-up view of the flower spike.

Drawings were made using conventional techniques and although the leaf and flower colors may appear different from the actual colors due to light reflectance, they are as accurate as possible by conventional photography.

BOTANICAL DESCRIPTION OF THE PLANT

The following is a detailed botanical description of the *Lavandula* cultivar named 'SUGARBERRY RUFFLES'. Data was collected in Arroyo Grande, Calif. from 9-month-old plants greenhouse grown in 16 cm. containers. Color determinations are made in accordance with the 2001 Royal Horticultural Society Colour Chart of London, England, except where general color terms of ordinary dictionary significance are used. The growing requirements are similar to the species.

Classification:

*Botanical classification.*—*Lavandula stoechas* 'SUGARBERRY RUFFLES'.
*Family.*—Lamiaceae.
*Genus.*—*Lavandula.*
*Species.*—*stoechas.*
*Variety denomination.*—'SUGARBERRY RUFFLES'.
*Common name.*—Lavender.

Plant:

*Habit.*—Dense.
*Height* (*at maturity*).—60 cm.
*Width* (*at maturity*).—70 cm.
*Life cycle.*—Perennial.
*Use.*—Ornamental for container or landscape.
*Vigour.*—Moderate.
*Hardiness.*—USDA Zone 8.
*Propagation.*—Tip and stem cuttings.
*Root system.*—Fibrous.
*Cultural requirements.*—Full sun, adequate but not excess water, and well-draining soil.
*Time to produce a rooted cutting.*—4–6 weeks.
*Time to produce a* 10 *cm. container plant in bloom.*—20 weeks.
*Seasonal interest.*—Flower spikes in spring and summer.
*Parentage.*—*Lavandula stoechas* 'SUGARBERRY RUFFLES' is a selection that resulted from controlled cross-pollination of the following parents: Female parent plant: *Lavandula stoechas* 'Kew Red'. Male parent plant: *Lavandula stoechas* 'Pukehou'.
*Disease and insect resistance.*—Minimal disease and insect susceptibility with occasional aphids on new growth.

Stem:

*Branching.*—Upright.
*Stem shape.*—Quadrangular.
*Stem surface.*—Pubescent.
*Pubescence color.*—156D.
*Stem color.*—Individual colors 199A and N144A.
*Stem length.*—Range of 8 cm to 10 cm.
*Stem width.*—3 mm.
*Stem fragrance.*—Resinous scent.
*Internode length.*—Range of 0.50 cm. to 1.50 cm.

Foliage:

*Leaf arrangement.*—Combination of whorled and opposite.
*Leaf division.*—Simple.
*Leaf shape.*—Elongated oblong.
*Leaf margin.*—Entire.
*Leaf apex.*—Apiculate and acute individual present.
*Leaf base.*—Truncate.
*Leaf attachment.*—Sessile.
*Leaf color* (*adaxial surface*).—138A.
*Leaf color* (*abaxial surface*).—138B.
*Leaf surface* (*adaxial surfaces*).—Pubescent.
*Color of hairs.*—156D.
*Venation.*—Reticulate.
*Vein color* (*adaxial surface*).—138A.
*Vein color* (*abaxial surface*).—138B.
*Leaf length.*—Range of 1.75 cm to 4 cm.
*Leaf width.*—Range of 0.20 cm. to 0.70 cm.
*Leaf fragrance.*—Resinous scent.

Inflorescence:

*Fragrance.*—Resinous scent.
*Blooming period.*—April through August.
*Inflorescence type.*—Spike.
*Spike length.*—3.50 cm.
*Spike diameter.*—2.25 cm.
*Spike shape.*—Conical.
*Inflorescent quantity.*—Range of 65–70 per container plant.

*Peduncle length.*—4.20 cm.
*Peduncle width.*—2 cm.
*Peduncle shape.*—Quadrangular.
*Peduncle color.*—N144B.
*Peduncle surface.*—Tomentose.
*Tomenta color.*—156D.
*Bud dimensions.*—3 mm in length and 1.50 mm in width.
*Bud shape.*—Ovoid.
*Bud color.*—N77A.
*Bud surface.*—Lanate.
*Bud apex.*—Acute.
(*Individual flower is referred to as corolla*).—Corolla number: Average of 16 on an individual spike. Corolla color: 70A or 72A or 72B. Corolla shape: Salverform. Corolla depth: 7 mm. Corolla diameter: 4 mm. Corolla tube depth: 5 mm. Corolla tube diameter: 1.50 mm. Petals: Four in number. Petals fused or unfused: Basally fused. Petal shape: Orbicular. Petal length: 1.50 mm. Petal width: 1.50 mm. Petal apex: Obtuse and emarginated petal apices individually observed on an individual corolla. Petal margin: Entire. Petal surfaces (adaxial and abaxial): Glabrous. Petal color (adaxial and abaxial surfaces): 70A or 72A or 72B. Calyx color: Individual colors N77A and 144A. Calyx shape: Tubular. Calyx surface: Lanate. Color of hairs: 155B. Calyx length: 5 mm. Calyx width: 2 mm. Sepals: Four in number. Sepals fused or unfused: Fused along three quarters of the length. Sepal apex: Acute.
(*Fertile bract*).—Fertile bract shape: Deltoid with tapered base. Quantity: Average of 20 per inflorescence. Fertile bract length: 0.50 cm. Fertile bract width: 0.60 cm. Fertile bract color (ventral and dorsal surface): Individual colors 144A, 77A and N77A. Vein pattern: Reticulate. Vein color (ventral and dorsal surfaces): Individual colors 77A and N77A. Fertile bract apex: Acuminate. Fertile bract base: Broadly attenuate. Fertile bract surfaces (ventral and dorsal): Lanate. Fertile bract margin: Entire.
(*Sterile bract*).—Sterile bracts: Range of 4–5 per inflorescence. Sterile bract form: Petaloid. Sterile bract appearance: Irridescent. Sterile bract arrangement: Whorled. Sterile bract surfaces (abaxial and adaxial): Pubescent. Color of hairs: 155B. Sterile bract shape: Broadly oblanceolate. Sterile bract margin: Entire. Sterile bract length: Average 2.25 cm. Sterile bract width: Average 1 cm. Sterile bract apex: Broadly acute. Sterile bract base: Aequilateral. Sterile bract color (abaxial and adaxial surfaces): 72B and 72C fading to 75B and 76B. Vein pattern: Reticulate. Vein color (abaxial and adaxial surfaces): 77A.

Reproductive organs:
*Stamens.*—Four in number.
*Stamen form.*—Adnate to ventral surface of corolla tube.
*Stamen color.*—155C.
*Stamen length.*—5 mm.
*Anther.*—Four.
*Anther color.*—161A.
*Pollen color.*—161C.
*Pollen quantity.*—Moderate.
*Pistil.*—One.
*Pistil length.*—3 mm.
*Pistil color.*—155B.
*Stigma height.*—Less than 0.50 mm.
*Stigma surface.*—Glossy.
*Stigma shape.*—Orbicular.
*Stigma color.*—79A.
*Ovary dimensions.*—Less than 0.50 mm.
*Ovary shape.*—Globose.
*Ovary color.*—138A.
*Ovary position.*—Superior.

Seed: No seed has been observed to date.

What is claimed is:

1. A new and distinct variety of *Lavandula* plant named 'SUGARBERRY RUFFLES' as described and illustrated herein.

* * * * *